(12) United States Patent
Lin et al.

(10) Patent No.: US 9,314,419 B2
(45) Date of Patent: Apr. 19, 2016

(54) ORAL CARE COMPOSITIONS WITH A REDUCED BITTER TASTE PERCEPTION

(71) Applicant: The Procter & Gamble Company, Cincinnati, OH (US)

(72) Inventors: Yakang Lin, Liberty Township, OH (US); Koti Sreekrishna, Mason, OH (US); John Christian Haught, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/633,163

(22) Filed: Feb. 27, 2015

(65) Prior Publication Data
US 2015/0306015 A1 Oct. 29, 2015

Related U.S. Application Data

(60) Provisional application No. 62/065,866, filed on Oct. 20, 2014, provisional application No. 61/945,437, filed on Feb. 27, 2014.

(51) Int. Cl.
| | | |
|---|---|---|
| *A61K 8/84* | (2006.01) | |
| *A61K 8/49* | (2006.01) | |
| *A61K 8/362* | (2006.01) | |
| *A61K 8/46* | (2006.01) | |
| *A61K 8/21* | (2006.01) | |
| *A61K 8/27* | (2006.01) | |
| *A61K 8/29* | (2006.01) | |
| *A61Q 11/00* | (2006.01) | |

(52) U.S. Cl.
CPC ... *A61K 8/84* (2013.01); *A61K 8/21* (2013.01); *A61K 8/27* (2013.01); *A61K 8/29* (2013.01); *A61K 8/362* (2013.01); *A61K 8/463* (2013.01); *A61K 8/4926* (2013.01); *A61Q 11/00* (2013.01); *A61K 2800/5426* (2013.01); *A61K 2800/592* (2013.01)

(58) Field of Classification Search
USPC .......................................... 514/724
See application file for complete search history.

(56) References Cited

U.S. PATENT DOCUMENTS

2009/0018213 A1* 1/2009 Snyder et al. ................. 514/724
2013/0243935 A1 9/2013 Barnekow et al.

OTHER PUBLICATIONS

U.S. Appl. No. 14/633,160, filed Feb. 27, 2015, Lin et al.
U.S. Appl. No. 14/633,161, filed Feb. 27, 2015, Lin et al.

* cited by examiner

*Primary Examiner* — Walter Webb
(74) *Attorney, Agent, or Firm* — Alexandra S. Anoff

(57) ABSTRACT

An oral care composition with reduced bitterness containing polyquaternium-2, polyquaternium-17, and/or polyquaternium-18.

20 Claims, 9 Drawing Sheets

ORAL CARE COMPOSITIONS WITH A REDUCED BITTER TASTE PERCEPTION

FIELD OF THE INVENTION

The present invention relates to an oral care composition comprising a low molecular weight polyquaternium to modulate bitterness, more particularly a low level of polyquaternium-2, polyquaternium-17, and/or polyquaternium-18 to modulate bitterness.

BACKGROUND OF THE INVENTION

There are five recognized taste sensations, sweet, salty, sour, bitter, and umami. Many people dislike things that are overly bitter and perceive it is as unpleasant, sharp, or otherwise disagreeable. Bitterness is the most sensitive of the tastes and it is thought to be a defense mechanism to protect the body against ingestion of toxic substances, as a large number of natural bitter compounds are known to be toxic.

However some components that are found in oral care compositions can often have a bitter and astringent taste associated with them. Specifically, metal salts have a high degree of astringency and bitterness when delivered from oral care compositions such as a dentifrice or mouthwash. Furthermore, hops, which can be used as an antimicrobial in oral care compositions can also have a bitter taste. Oral care compositions often contain flavors and sweeteners to mute the bitterness associated with the actives and excipients. Despite these efforts, many oral care compositions still possess an unpleasant taste and/or after taste. This causes some consumers to avoid and/or dislike using oral care compositions.

Thus, there is a need for an oral care composition with reduced bitterness.

SUMMARY OF THE INVENTION

An oral care composition with reduced bitterness comprising a polyquaternium selected from the group consisting of polyquaternium-2, polyquaternium-17, polyquaternium-18, and combinations thereof.

An oral care composition with reduced bitterness comprising: (a) a polyquaternium selected from the group consisting of polyquaternium-2, polyquaternium-17, polyquaternium-18, and combinations thereof; (b) a fluoride compound; (c) a metal salt; wherein the oral care composition is a dentifrice.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1A:
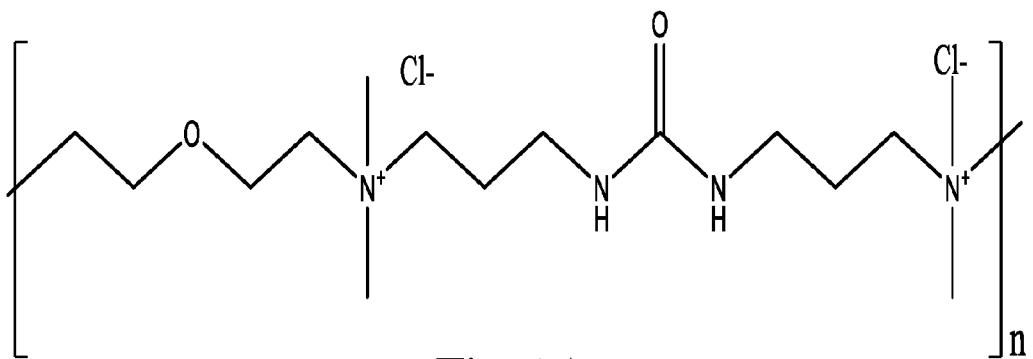
FIG. 1A shows the molecular structure for polyquaternium-2.

Oral care compositions, particularly mouthwashes, floss, tooth strips, dentures, and dentifrices, have a bitter and astringent taste associated with them due to the components, such as metal salts, binders, thickeners, and antimicrobial agents like, but not limited to hops, thymol, cetyl pyridinium chloride (CPC), triclosan, and stannous fluoride It has been surprisingly found that polyquaternium-2 can significantly modulate the bitterness in some oral care compositions.

Several polymers, including other polyquats, were tested in vitro taste bud cell assays to determine whether they may serve as a bitter blocker. Polyquaternium-2 modulated the bitterness of guaifenesin (GG) in the cell assays better than any other polymer, including the polyquats which have a similar chemical structure. Polyquaternium-17 and/or polyquaternium-18 are structurally analogous to polyquaternium-2 and can be used instead of or in combination with polyquaternium-2. GG, a drug used in over-the-counter medication, was selected as a compound for screening bitter blockers because it is known for being exceptionally bitter and difficult to taste mask with sweeteners and flavors.

After polyquaternium-2 was selected as a potential bitter modifier, different strains of hops were tested in vitro using taste bud cell assays. Surprisingly, it was found that polyquaternium-2 reduced the bitterness of hops. Polyquaternium-17 and/or polyquaternium-18 may also reduce the bitterness of hops.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

The composition can contain, consist of, or consist essentially of, the essential elements and limitations of the invention described herein, as well as any additional or optional ingredients, components, or limitations described herein or otherwise useful in oral care compositions.

As used herein, the word "include," and its variants, are intended to be non-limiting, such that recitation of items in a list is not to the exclusion of other like items that may also be useful in the materials, compositions, devices, and methods of this invention.

As used herein, the word "or" when used as a connector of two or more elements is meant to include the elements individually and in combination; for example X or Y, means X or Y or both.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

As used herein, the articles "a" and "an" are understood to mean one or more of the material that is claimed or described, for example, "an active" or "a solvent".

The compositions of the present invention can contain, consist of, or consist essentially of, the essential elements and limitations of the invention described herein, as well as any additional or optional ingredients, components, or limitations described herein or otherwise useful in dosage forms intended for use or consumption by humans.

Figure 1B:
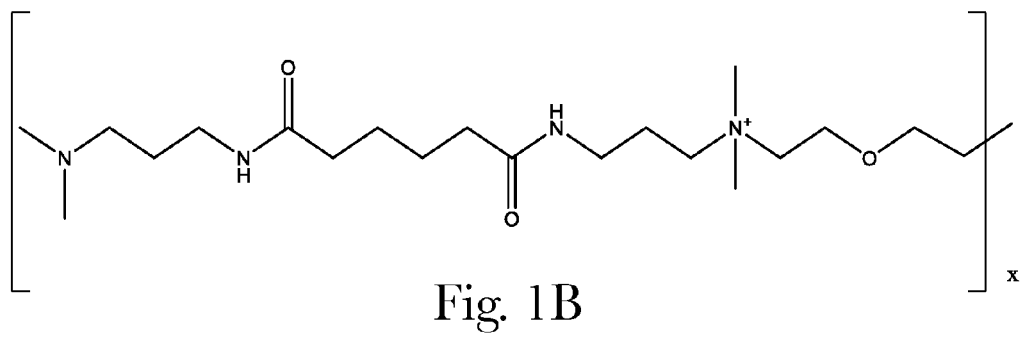
FIG. 1B shows the molecular structure for polyquaternium-17.
Figure 1C:
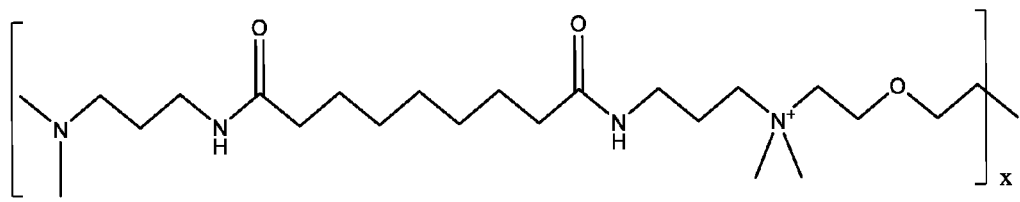
FIG. 1C shows the molecular structure for polyquaternium-18.

It has been found that polyquaternium-2 can be added to compositions, particularly oral care compositions to reduce bitterness. Polyquaternium-2 has the CAS Registry Number 68555-36-2 and the chemical name is Poly[bis(2-chloroethyl)ether-alt-1,3-bis[3-(dimethylamino)propyl]urea] and is commercially available as Mirapol® A 15 (available from Rhodia, Cranbury, N.J.). The molecular structure for polyquaternium-2 is shown in FIG. 1A. Polyquaternium-17 (CAS Registry Number 148506-50-7) and polyquaternium-18 (CAS Registry Number 113784-58-0) are structurally analogous to polyquaternium-2 and can be used in addition to or instead of polyquaternium-2 to modulate bitter. The molecular structure for polyquaternium-17 is shown in FIG. 1B and the molecular structure for polyquaternium-18 is shown in FIG. 1C.

Figure 2A:
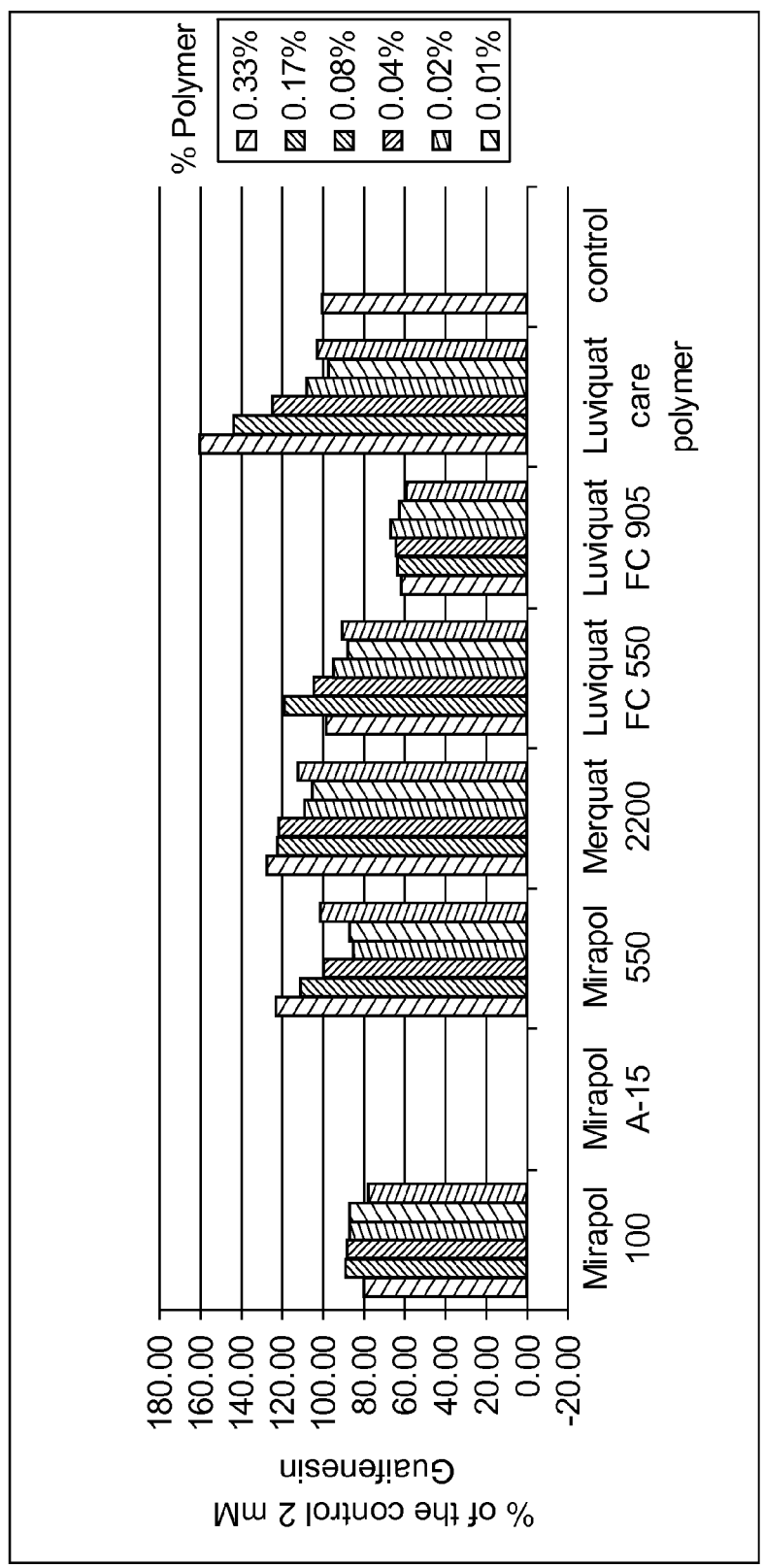
FIG. 2A compares the modulation of bitterness of solutions with different water soluble polymers in an Assay for Taste Receptors.

FIG. 2A compares the modulation of bitterness of a control solution comprising 2 mM guaifenesin (GG) with solutions comprising 2 mM GG and one of seven water soluble polymers at concentrations ranging from 0.33% to 0.01%. The results for FIG. 2 are from an in vitro Assay for Taste Receptors, as described hereafter. The cell cultures and assays provide an in vitro method to screen for bitterness that can mimic an in vivo response.

The water soluble polymers that were tested were as follows at concentrations ranging from 0.01% to 0.33%:
Polyquaternium-6 commercially available as Mirapol® 100 [CAS#26062-79-3] (available from Rhodia, Cranbery, N.J.)
Polyquaternium-2 commercially available as Mirapol® A 15 [CAS#68555-36-2] (available from Rhodia, Cranbury, N.J.)
Polyquaternium-7 commercially available as Mirapol® 550 [26590-05-6] (available from Rhodia, Cranbury, N.J.)
Polyquaternium-7 commercially available as Merquat™ 2200 [CAS#26590-05-6] (available from Lubrizol, Deer Park, Tex.)
Polyquaternium-16 commercially available as Luviquat® FC550 [CAS#95144-24-4] (available from BASF, Florham Park, N.J.)
Polyquaternium D16 commercially available as Luviquat® FC905 [CAS#95144-24-4] (available from Crescent Company, Islandia, N.Y.)
Polyquaternium-44 commercially available as Luviquat® care polymer [CAS#150599-70-5] (available from BOC Sciences, Shirley, N.Y.)

The taste receptors were activated as described in the Assay for Taste Receptors herein. The observed activation is presented as a % of the control value. The control value is activation by a 2 mM GG solution with no added polymers. The results from this assay showed that only Polyquaternium-2 completely blocked the activation of taste cell receptors by GG. This is especially surprising, since GG is one of the most bitter actives used in liquid medications. Other polymers, including polyquaternium-6 and polyquaternium D16 (Luviquat® 905) also showed some reduction, however the modulation was not dose dependent.

Figure 2B:
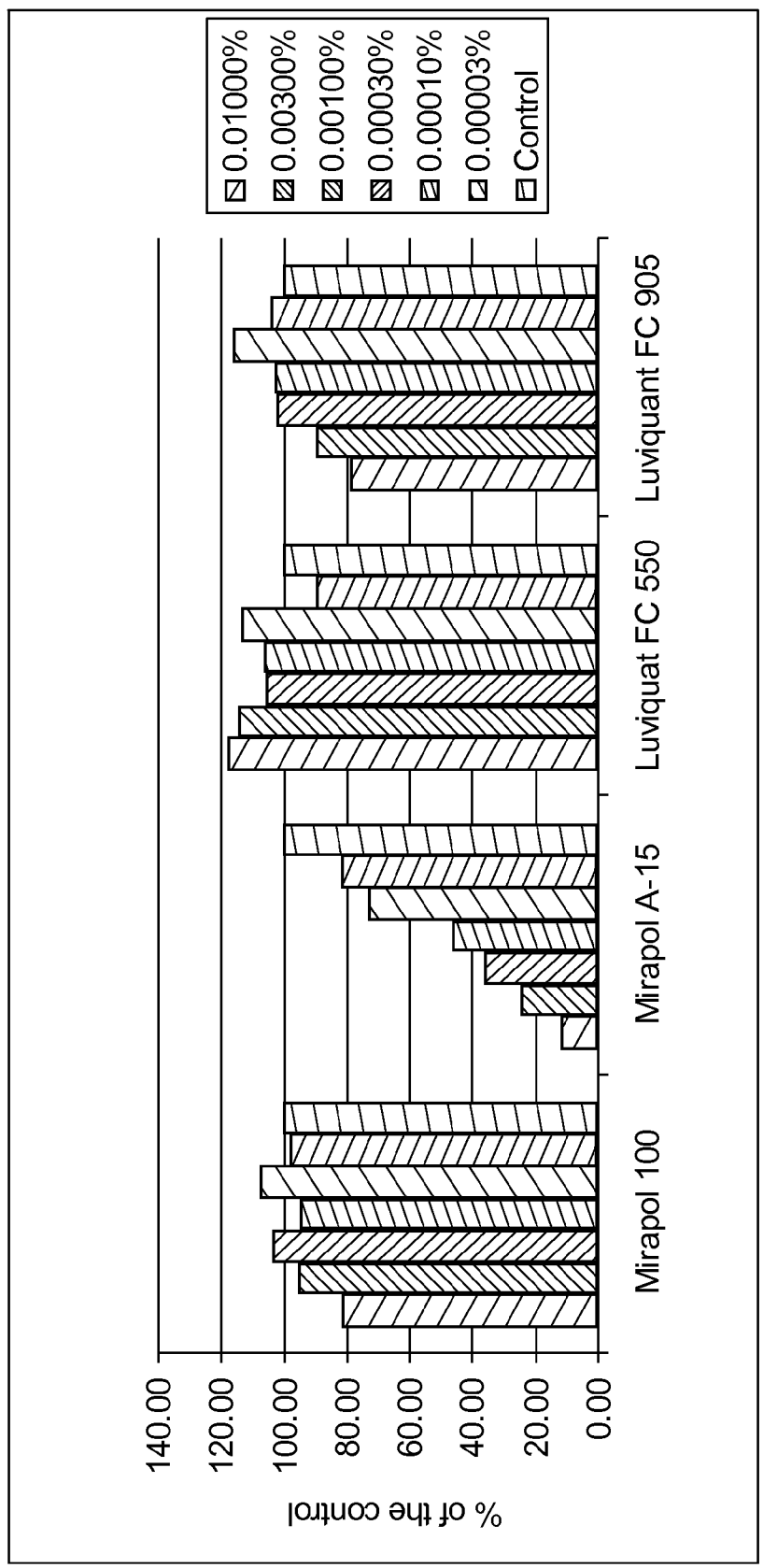
FIG. 2B compares the modulation of bitterness of solutions with different water soluble polymers in an Assay for Taste Receptors.

FIG. 2B compares the modulation of bitterness of a solution comprising 2 mM GG with one of four water soluble polymers at concentrations ranging from 0.01% to 0.00003%. The four water soluble polymers were polyquaternium-6 (Mirapol® 100), polyquaternium-2 (Mirapol® A15), polyquaternium D16 (Luviquat® FC 550), and polyquaternium D16 (Luviquat® FC 905). The same Assay for Taste Receptor Method described herein and for FIG. 2 was used to generate the results for FIG. 3A. The lower concentrations of polymer were selected to help further differentiate the potential ability for the polymers to provide bitter blocking in vivo.

Again, polyquaternium-2 provided the greatest reduction in bitterness of the 2 mM GG solution. At 0.01%, the bitterness was reduced to less than 20% of the bitterness of the control. Furthermore, polyquaternium-2 was the only composition that showed dose dependent blocking.

Figure 2C:
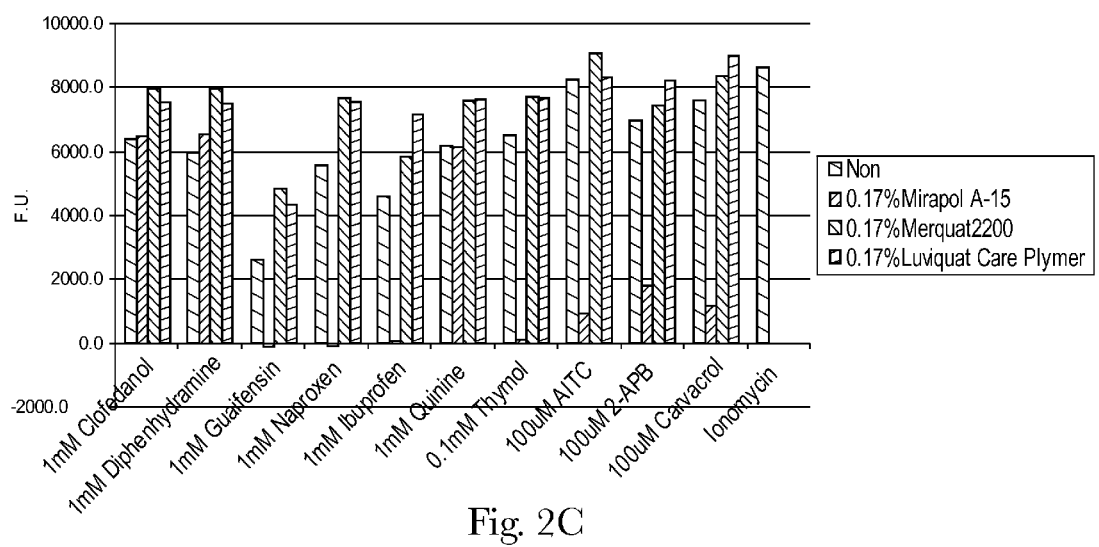
FIG. 2C compares the modulation of bitterness of solutions with different water soluble polymers and actives in an Assay for Taste Receptors.

FIG. 2C compares the modulation of bitterness of a solutions containing different substances that are known to be bitter with 0.17% polyquaternium-2 (Mirapol® A 15), polyquaternium-7 (Merquat™ 2200), and polyquaternium-44 (Luviquat® Care Polymer). The Assay for Taste Receptor Method described herein and was used to generate the results for FIG. 2C. The substances that were tested were 1 mM clofedanol, 1 mM diphenhydramine, 1 mM GG, 1 mM naproxen, 1 mM ibuprofen, 1 mM quinine, 0.1 mM thymol, 100 µM AITC (Allyl Isothiocyanate), 100 µM APB (2-Aminoethoxydiphenyl borate), 100 µM carvacrol, and 10 µM ionomycin was used as the control.

Surprisingly, the polyquaternium-2 blocked all but three of the known bitter molecules, whereas the higher molecular weight polyquats, polyquaternium-7, and polyquaternium-44, did not show bitter blocking. Instead the polyquaternium-7, and polyquaternium-44 caused an increase in the bitter response relative to each bitter molecule, as shown by the higher fluorescence units (FUs).

Figure 3A:
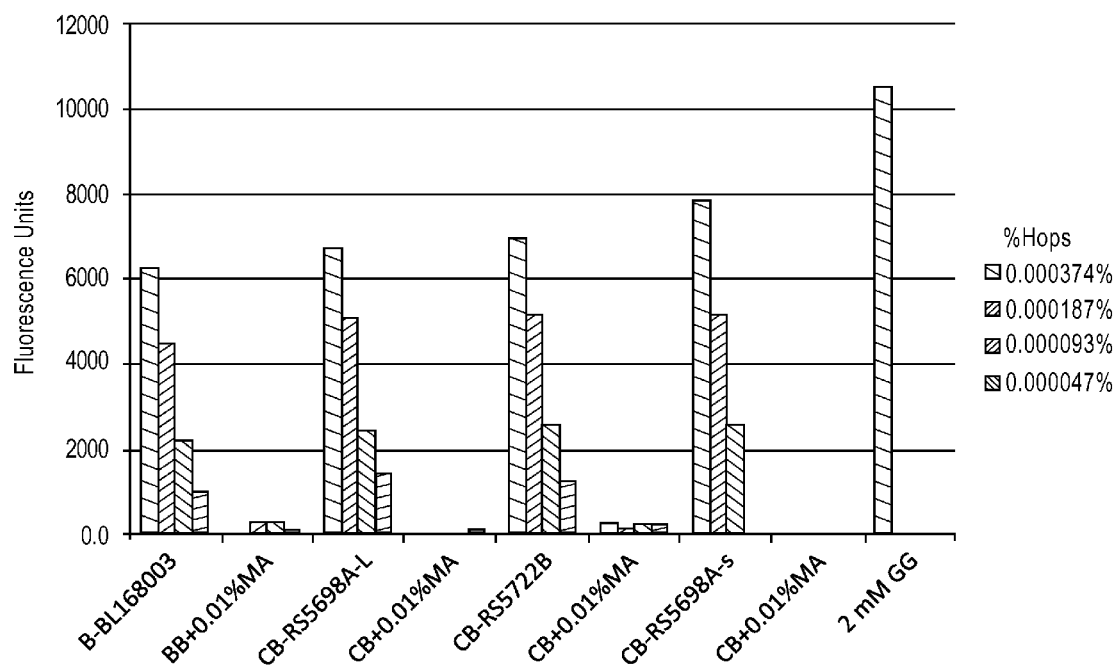
FIG. 3A compares the modulation of bitterness of different strains of hops with polyquaternium-2 in an Assay for Taste Receptors.
Figure 3B:
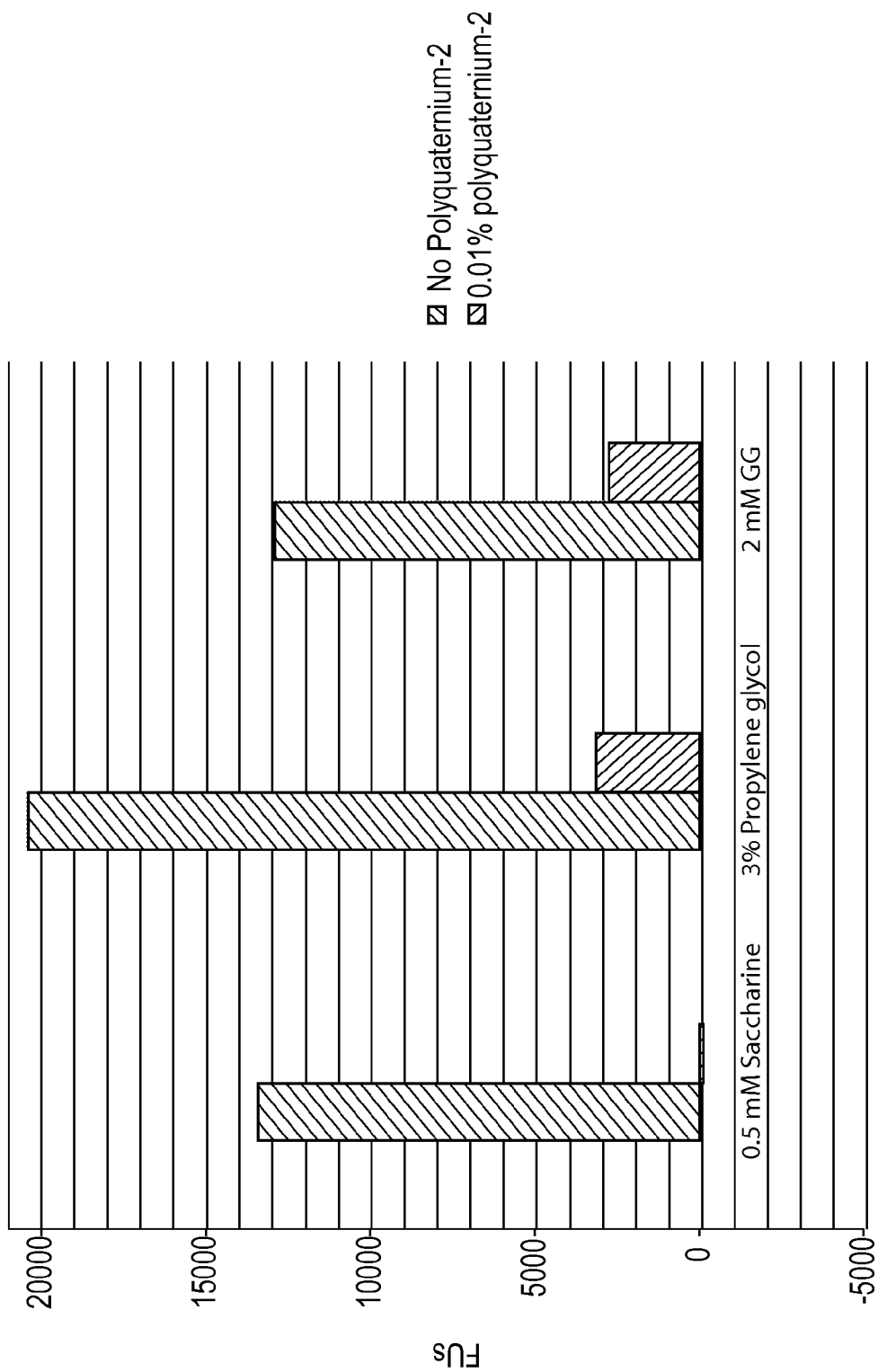
FIG. 3B compares the modulation of bitterness of different compositions with polyquaternium-2 in an Assay for Taste Receptors.

Since polyquaternium-2 was effective in blocking the bitterness in the Assay for Taste Receptors, it was desirable to understand if polyquaternium-2 was effective against other bitter agents. As shown in FIGS. 3A and 3B, it was found that polyquaternium-2 was also effective at blocking bitterness from hops, propylene glycol, and saccharin in the Assay for Taste Receptors.

FIG. 3A compares the modulation of bitterness of solutions containing a strain of hops at different concentrations ranging from 0.000047% to 0.000374%. Each strain of hops was tested with the addition of 0.01% polyquaternium-2. The following strains of hops were tested: B-BL168003, CB-RS5698A-L, CB-RS5722B, and CB-RS5698A-s. All strains of hops used in this example are commercially available from available from Hopsteiner®, Yakima, Wash. 2 mM GG was used as a control to make sure that the bitter cells were registering bitterness. The results for FIG. 3A are from an in vitro Assay for Taste Receptors as described hereafter.

Surprisingly, as seen in FIG. 3A, 0.01% polyquaternium-2 significantly reduces the bitterness of all four strains of hops. At many concentrations and strains, the bitterness was not detectable by the bitter cells, which could mimic an in vivo response.

FIG. 3B compares the modulation of bitterness, if any, of solutions containing a composition and 0.01% polyquaternium-2 in the in vitro Assay for Taste Receptors as described hereafter. The compositions tested were 0.5 mM saccharin, 3% propylene glycol, and 2 mM GG was used as the control. Surprisingly, polyquaternium-2 completely blocked the bitterness from saccharin and substantially reduced the bitterness of both propylene glycol.

In one example, the oral care composition can contain from about 0.0001% to about 5% hops, in another example from about 0.001% to about 2.5%, in another example from about 0.01% to about 1%, in another example from about 0.05% to about 0.5%, and in another example from about 0.1% to about 0.2%. The composition can contain alpha hops and/or beta hops.

In one example polyquaternium-2, polyquaternium-17, and/or polyquaternium-18 reduces the overall bitterness of a composition by at least about 5% as compared to an identical composition without the polyquaternium-2, polyquaternium-17, and/or polyquaternium-18 as determined by the in vitro Assay for Taste Receptors as described hereafter, in another example by at least about 10%, in another example by at least about 20%, in another example by at least about 30%, in another example by at least about 40%, in another example by at least about 50%, in another example by at least about 60%, in another example by at least about 65%, in another example by at least about 70%, in another example by at least about 75%, in another example by at least about 80%, in another example by at least about 85%, in another example by at least about 90%, in another example at least about 93%, in another example at least about 95%, in another example by at least about 97%, in another example by at least about 98%, in another example by at least about 99% and in another example by at least about 100%.

In another example, polyquaternium-2, polyquaternium-17, and/or polyquaternium-18 can reduce the overall bitterness of a composition as compared to an identical composition without the polyquaternium-2, polyquaternium-17, and/ or polyquaternium-18 as determined by the in vitro Assay for Taste Receptors as described hereafter.

In another example, the composition can have an overall bitterness of less than about 8000 fluorescence units (FUs) as determined by the in vitro Assay for Taste Receptors as described hereafter, in another example less than about 7500 FUs, in another example less than about 70000 FUs, in another example less than about 6500 FUs, in another example less than about 6000 FUs, in another example less than about 5500 FUs, in another example less than about 5000 FUs, in another example less than about 4500 FUs, in another example less than about 4000 FUs, in another example less than about 3500 FUs, in another example less than about 3000 FUs, in another example less than about 2500 FUs, in another example less than about 2000 FUs, in another example less than about 1500 FUs, in another example less than about 1000 FUs, in another example less than about 750 FUs, in another example less than about 500 FUs, in another example less than about 350 FUs, in another example less than about 300 FUs, in another example less than about 250 FUs, in another example less than about 200 FUs, in another example less than about 150 FUs, in another example less than about 100 FUs, and in another example less than about 50 FUs.

Figure 4A:
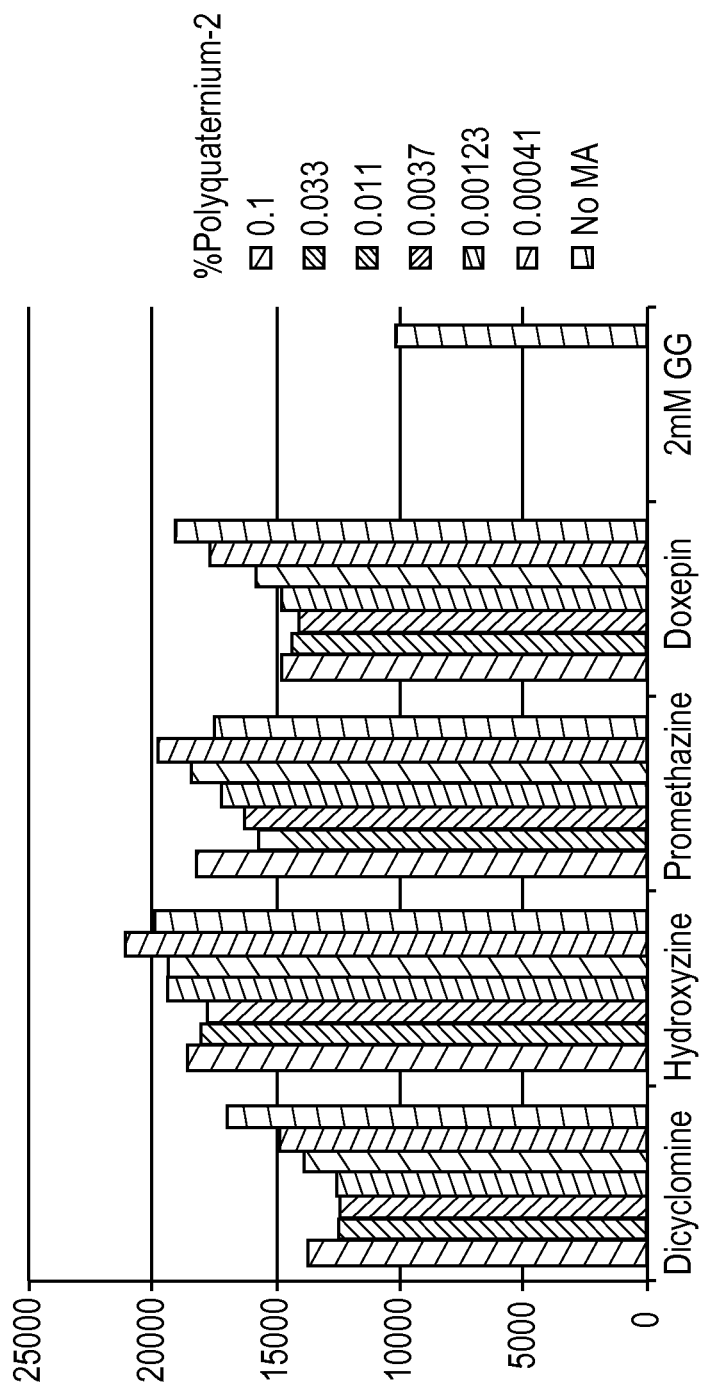
FIG. 4A compares the modulation of bitterness of solutions containing an active and a concentration of polyquaternium-2 in an Assay for Taste Receptors.
Figure 4B:
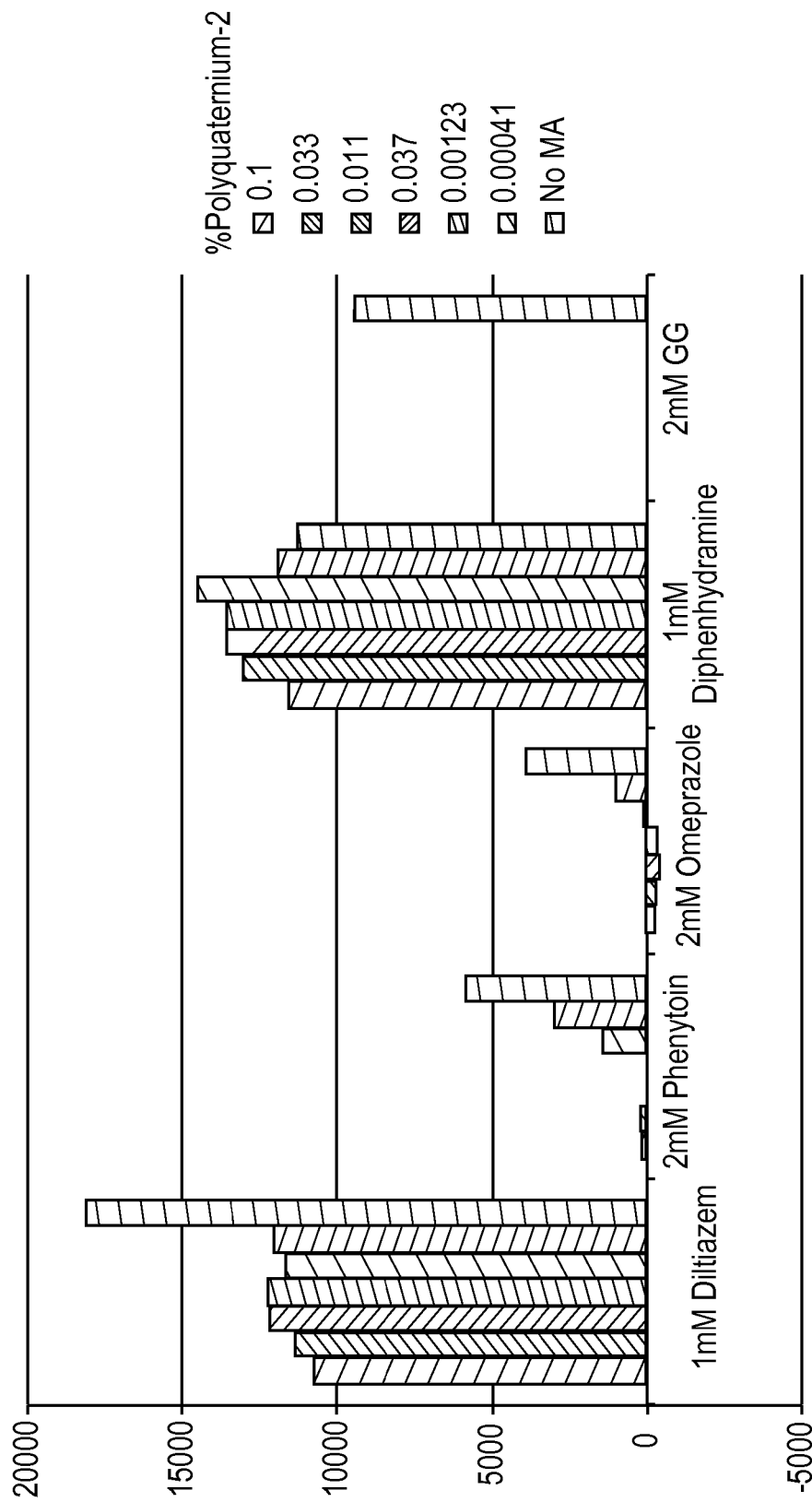
FIG. 4B compares the modulation of bitterness of solutions containing an active and a concentration of polyquaternium-2 in an Assay for Taste Receptors.
Figure 4C:
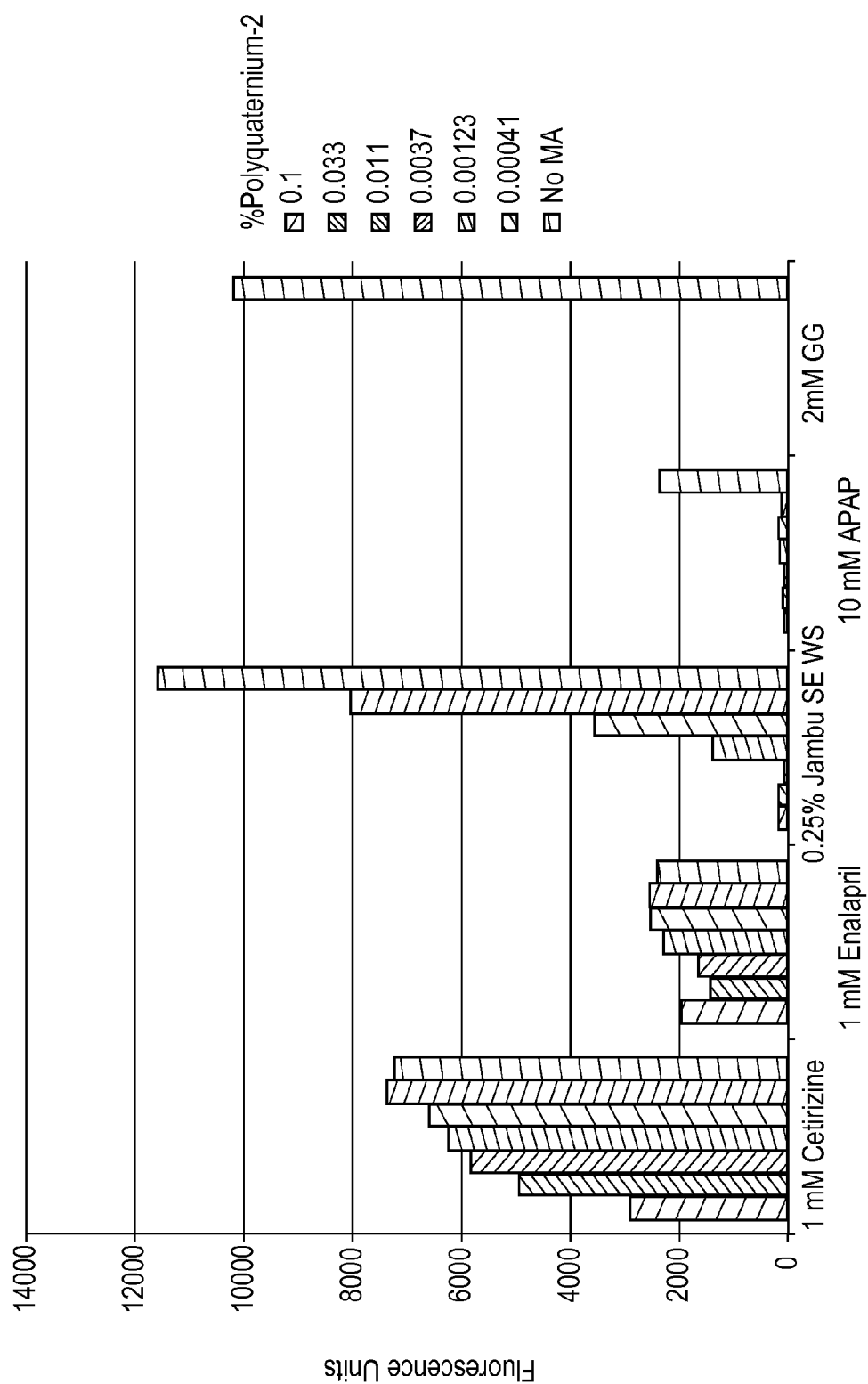
FIG. 4C compares the modulation of bitterness of solutions containing an active and a concentration of polyquaternium-2 in an Assay for Taste Receptors.

However, it has been surprisingly discovered that polyquaternium-2 does not modulate the bitterness for all compounds that are known to be bitter. For instance, FIGS. 4A, 4B, and 4C compare the modulation of bitterness, if any, of solutions containing an active and a concentration of polyquaternium-2. The concentration of polyquaternium-2 ranges from 0.00041% to 0.1%. GG at a concentration of 2 mM without polyquaternium-2 is used as a control. The actives were selected because they are frequently used in medications and are known to be bitter. The results for FIGS. 4A, 4B, and 4C are from an in vitro Assay for Taste Receptors as described hereafter.

FIG. 5A compares the modulation of bitterness, if any, of solutions comprising 250 μM active and a concentration of polyquaternium-2. The actives in FIG. 4A are dicyclomine, hydroxyzine, promethazine, doxepin, and 2 mM GG. FIG. 5A shows that polyquaternium-2 has at best a very weak bitter blocking activity on dicyclomine, hydroxyzine, promethazine, and doxepin. However, FIG. 4A does not show a dose dependent effect and thus polyquaternium-2 is probably not a specific blocker of these compositions.

The actives in FIG. 5B are 1 mM diltiazem, 2 mM phenytoin, and 1 mM diphenhydramine. Polyquaternium-2 blocked some of the bitterness of diltiazem, but it doesn't show a dose dependent effect and thus polyquaternium-2 is probably not a specific blocker for diltiazem. Polyquaternium-2 strongly blocked the bitterness from phenytoin and omeprazole and polyquaternium-2 had little or no effect on diphenydramine.

The actives tested in FIG. 4C included 1 mM cetirizine, 1 mM enalapril, 0.25% jambu (*Acmella oleracea*) extract (commercially available as Jambu SE WS from Naturex™, South Hackensack, N.J.), and 10 mM acetaminophen (APAP). Polyquaternium-2 blocked some of the bitterness of cetirizine. Polyquaternium-2 did not show a dose dependent bitter blocking of enalapril. However, polyquaternium-2 shows a strong dose dependent effect on blocking jambu and APAP.

Polyquaternium-2, polyquaternium-17, and/or polyquaternium-18 can be added to compositions, in particular oral care compositions. In one example, the composition contains from about 0.01% to about 1% polyquaternium-2, polyquaternium-17, and/or polyquaternium-18, in another example from about 0.03% to about 0.3%, in another example from about 0.05% to about 0.2%, in another example from about 0.07% to about 0.15%, in another example from about 0.08% to about 0.13%, and in another example from about 0.09% to about 0.11. In one example, the composition can contain about 0.1% polyquaternium-2, polyquaternium-17, and/or polyquaternium-18. In another example, the composition can contain less than about 1% polyquaternium-2, polyquaternium-17, and/or polyquaternium-18, in another example less than about 0.5%, in another example less than about 0.3%, in another example less than about 0.2%, in another example less than about 0.15%, and in another example less than about 0.12%.

In one example, polyquaternium-2, polyquaternium-17, and/or polyquaternium-18 can be added to the oral care composition. For instance, the dentifrice or mouthwash can contain polyquaternium-2, polyquaternium-17, and/or polyquaternium-18. In another example, polyquaternium-2, polyquaternium-17, and/or polyquaternium-18 can be simultaneously with the oral care composition. In another example, polyquaternium-2, polyquaternium-17, and/or polyquaternium-18 can be administered before the oral care composition. In one example the polyquaternium-2, polyquaternium-17, and/or polyquaternium-18 can be administered immediately before the oral care composition and in one example the polyquaternium-2, polyquaternium-17, and/or polyquaternium-18 can be administered and then a period of time can pass before using the oral care composition.

In one example, polyquaternium-2, polyquaternium-17, and/or polyquaternium-18 can be added to an oral care composition intended for use by children. Children can be especially sensitive to bitter tastes and adding polyquaternium-2, polyquaternium-17, and/or polyquaternium-18 can make bitter compositions, more palatable, especially to children.

Actives and other ingredients may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the oral care composition.

It is common to have a fluoride compound present in dentifrices and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 to Briner et al. and U.S. Pat. No. 3,678,154 to Widder et al.

Stannous salts include stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients used to stabilize the stannous may be included, such as the ingredients described in Majeti et al. and Prencipe et al.

Zinc salts include zinc fluoride, zinc chloride, zinc iodide, zinc chlorofluoride, zinc acetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof.

In one example, the copper salt can be selected from copper fluoride, copper chloride, copper iodide, copper chlorofluoride, copper acetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further example, the copper salt can be selected from copper gluconate, copper acetate, copper glycinate, and combinations thereof.

Alkali metal bicarbonate salts are soluble in water and unless stabilized, tend to release carbon dioxide in an aqueous system. Sodium bicarbonate, also known as baking soda, can be the preferred alkali metal bicarbonate salt. The alkali metal bicarbonate salt also functions as a buffering agent. Because of the pH at which alkali metal bicarbonate salts buffer, the bicarbonate salt may be in a phase separate from the stannous ion source. In certain examples, the oral care composition of the present invention may contain from about 0.5% to about 50%, from about 0.5% to about 30%, from about 2% to about 20%, or from about 5% to about 18% of an alkali metal bicarbonate salt, by weight of the oral care composition.

Some metal salts which may be used in the present invention, such as zinc chloride, zinc citrate, copper gluconate, and zinc gluconate, are also associated with an off taste described as dirty, dry, earthy, metallic, sour, bitter, and astringent.

Sweeteners include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

Rebiana can be a steviolglycoside from Cargill Corp., Minneapolis, Minn., which is an extract from the leaves of the *Stevia rebaudiana* plant (hereinafter referred to as "Rebiana"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable examples of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials include water, glycerin, sorbitol, polyethylene glycols having a molecular weight of less than about 50,000, propylene glycol and other edible polyhydric alcohols, ethanol, or combinations thereof. The oral care compositions of the present invention include from about 5% to about 80%, by weight of the composition, of a carrier material. In certain examples, the compositions contain carrier materials in an amount of from about 10% to about 40%, by total weight of the oral care composition.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoyl-stearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds include bis[4-(R-amino)-1-pyridinium]alkanes as disclosed in U.S. Pat. No. 4,206,215, Jun. 3, 1980, to Bailey and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, and flavor oils such as thymol. In another example, the antimicrobial agent can include triclosan.

The compositions of the present invention may contain antimicrobial agents in an amount of from about 0.035% or more, from about 0.1% to about 1.5%, from about 0.045% to about 1.0%, or from about 0.05% to about 0.10%, by total weight of the oral care composition.

Bleaching agents can include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. Some bleaching agents provide a burn sensation within an oral care composition, for example peroxides and percarbonates.

The compositions of the present invention may contain bleaching agents in an amount of from about 0.01% to about 30%, from about 0.1% to about 10%, or from about 0.5% to about 5%, by total weight of the oral care composition.

Surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein $Z_1$, $Z_2$, or $Z_3$ may be identical or different, at least one being an organic moiety, in one example selected from linear or branched, alkyl or alkenyl group of from 1 to 22 carbon atoms, optionally substituted by one or more phosphate groups; alkoxylated alkyl or alkenyl, (poly) saccharide, polyol or polyether group.

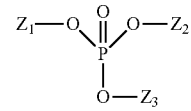

Some other organophosphate agents include alkyl or alkenyl phosphate esters represented by the following structure:

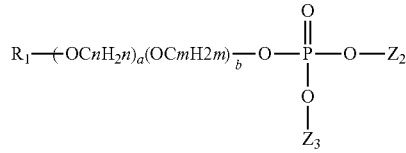

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z_2$ and $Z_3$ may be identical or different, each represents hydrogen, alkali metal, ammonium, protonated alkyl amine or protonated functional alkyl amine such as an alkanolamine, or a $R_1$-$(OC_nH_{2n})_a(OC_mH_{2m})_b$- group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one example, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention can include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio)

acetate, coco betaine or 2-(N-coco-N, N-dimethyl ammonio) acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these surfactants are soapy, bitter, chemical, or artificial.

Additional suitable polymeric organophosphate agents can include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation Impurities may include dodecanol, dodecanal, benzaldehyde, and other TRPA1 or TRPV1 agonists.

Cationic surfactants useful in the present invention can include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421 to Briner et al. Certain cationic surfactants can also act as germicides in the oral care compositions disclosed herein.

Examples of some flavors and flavor components that may be used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors are generally present in an amount of from about 0.4% to about 5% or from about 1% to about 3%, by total weight of the oral care composition.

Anti-tartar agents include pyrophosphate salts as a source of pyrophosphate ion. The pyrophosphate salts useful in the present compositions include, for example, the mono-, di- and tetraalkali metal pyrophosphate salts and combinations thereof. Disodium dihydrogen pyrophosphate ($Na_2H_2P_2O_7$), sodium acid pyrophosphate, tetrasodium pyrophosphate ($Na_4P_2O_7$), and tetrapotassium pyrophosphate ($K_4P_2O_7$) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying examples, the amount of pyrophosphate salt may be from about 1.5% to about 15%, from about 2% to about 10%, or about 3% to about 8%, by total weight of the oral care composition.

Examples of some colorants that may be used in oral care compositions include D&C Yellow No. 10, FD&C Blue No. 1, FD&C Red No. 40, D&C Red No. 33 and combinations thereof. In certain examples, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 0.8%, by weight of the oral care composition. The most well-known cooling sensate compound can be menthol, particularly L-menthol, which is found naturally in peppermint oil notably of *Mentha arvensis* L and Mentha *viridis* L. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there can be no cooling effect for the other isomers. For example, d-neomenthol is reported to have a cooling threshold of about 25,000 ppb and 1-neomenthol about 3,000 ppb.

Of the menthol isomers the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the p-menthanecarboxamide compounds such as N-ethyl-p-menthan-3-carboxamide, known commercially as "WS-3", and others in the series such as WS-5 (N-ethoxycarbonylmethyl-p-menthan-3-carboxamide), WS-12 (1R*,2S*)—N-(4-Methoxyphenyl)-5-methyl-2-(1-methylethyl)cyclohexanecarboxamide] and WS-14 (N-tert-butyl-p-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and p-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425 to Amano et al. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,917,613; 3,991,178; 5,703,123; 5,725,865; 5,843,466; 6,365,215; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112 and phosphine oxides as reported in U.S. Pat. No. 4,070,496.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. In certain examples, if the oral composition or particular phase comprises a polyphosphate having an average chain length of about 4 or more, calcium containing abrasives and alumina are not preferred abrasives.

Silica dental abrasives of various types are often used in oral care compositions due to their exceptional dental cleaning and polishing performance without unduly abrading tooth enamel or dentine. Silica abrasive polishing materials that may be used in the present invention, as well as other abrasives, generally have an average particle size ranging between about 0.1 to about 30 μm or from about 5 to about 15 μm. The abrasive can be precipitated silica or silica gels such as the silica xerogels described in Pader et al., U.S. Pat. No. 3,538,230 and DiGiulio, U.S. Pat. No. 3,862,307. Silica xerogels marketed under the trade name "Syloid" by the W.R. Grace & Company, Davison Chemical Division, Augusta, Ga. may be used. Also precipitated silica materials such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in Wason, U.S. Pat. No. 4,340,583; and Rice U.S. Pat. Nos. 5,589,160; 5,603,920; 5,651,958; 5,658,553; and 5,716,601.

Thickening material or binders may be used to provide a desirable consistency to the oral care compositions of the present invention. For example when the oral care compositions are in the form of dentifrices, topical oral gels, mouthrinse, denture product, mouthsprays, lozenges, oral tablets or chewing gums, the amount and type of the thickening material will depend upon the form of the product. Thickening materials include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. Thickening materials can be used in an amount from about 0.1% to about 15%, by weight of the oral care composition.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

Example 1

Examples 1A-1D are dentifrice compositions that may be prepared by conventional methods chosen by the formulator and illustrate dentifrice compositions containing polyquaternium-2. The compositions can exhibit reduced bitterness.

| Ingredient | Ex. 1A | 1B | 1C | 1D |
|---|---|---|---|---|
| FD&C Blue #1 Color Solution | 0.045% | 0.045% | 0.045% | 0.045% |
| Sodium Fluoride | 0.243% | 0.243% | 0.243% | 0.243% |
| CARBOMER 956 | 0.300% | 0.300% | 0.300% | 0.300% |
| Sodium Saccharin | 0.300% | 0.300% | 0.300% | 0.300% |
| Sodium Phosphate, Monobasic, Monohydrate | 0.419% | 0.419% | 0.419% | 0.419% |
| Titanium Dioxide | 0.525% | 0.525% | 0.525% | 0.525% |
| Carboxymethycellulose Sodium | 0.800% | 0.800% | 0.800% | 0.800% |
| Peppermint Flavor | 1.000% | 1.000% | 0% | 0% |
| Spearmint Flavor | 0% | 0% | 1.000% | 1.000% |
| Mirapol ® A 15[1] | 0% | 0.1% | 0% | 0.1% |
| Tribasic Sodium Phosphate Dodecahydrate | 1.100% | 1.100% | 1.100% | 1.100% |
| Sodium Lauryl Sulfate 28% Solution | 4.000% | 4.000% | 4.000% | 4.000% |
| Silica, Dental Type, NF (Zeodent 119) | 15.000% | 15.000% | 15.000% | 15.000% |
| SORBITOL SOLUTION LRS USP | 54.673% | 54.673% | 54.673% | 54.673% |
| Water Purified, USP, PhEur, JP, JSCI | Q.S. | Q.S. | Q.S. | Q.S. |

[1] Available from Rhodia, Cranbury New Jersey

Example 2

Examples 2A-2C are dentifrice compositions that may be prepared by conventional methods chosen by the formulator and illustrate dentifrice compositions containing polyquaternium-2. The compositions can exhibit reduced bitterness, especially bitterness from metals.

| Ingredient | 2A | 2B | 2C |
|---|---|---|---|
| Mica, Titanium Dioxide coated | 0.4% | 0.4% | 0.4% |
| Sodium Fluoride | 0.243% | 0.243% | 0.243% |
| Polyethylene Specks, Blue | 0.35% | 0.35% | 0.35% |
| Carrageenan | 0.7% | 0.7% | 0.7% |
| Sodium Saccharin | 0.300% | 0.300% | 0.300% |
| Titanium Dioxide | 0.525% | 0.525% | 0.525% |
| Carboxymethycellulose Sodium | 1.3% | 1.3% | 1.3% |
| Hydroxyethylcellulose | 0.3% | 0.3% | 0.3% |
| Peppermint Flavor | 1.000% | 1.000% | 1.000% |
| Added Menthol | 0% | 0.25% | 0.25% |
| Sodium Lauryl Sulfate 28% Solution | 1.0% | 1.0% | 1.0% |
| Silica, Dental Type, NF (Zeodent 119) | 17% | 17% | 17% |
| Sorbitol Solution LRS USP | 40.5% | 40.5% | 40.5% |
| Zinc Citrate Dihydrate | 0.788% | 0.788% | 0.788% |
| Stannous Chloride Dihydrate | 0.209% | 0.209% | 0.209% |
| Mirapol ® A 15[2] | 0% | 0.5% | 0.1% |
| G180 Coolant[3] | 0.025% | 0.010% | 0.010% |
| Vanillyl Butyl Ether | 0% | 0% | 0% |
| Zingerone | 0% | 0% | 0% |
| Frescolat MGA coolant | 0.0225% | 0.010% | 0.010% |
| WS-5 coolant | 0.007% | 0.010% | 0% |
| Sucralose | 0.2% | 0.2% | 0.2% |
| Water Purified, USP | Q.S. | Q.S. | Q.S. |

[2] Available from Rhodia, Cranbury New Jersey
[3] Available from Givaudan of Cincinnati, OH Example 3

Examples 3A-3B are mouthwash compositions that may be prepared by conventional methods chosen by the formulator and illustrate mouthwash compositions containing polyquaternium-2. The compositions can exhibit reduced bitterness.

| Ingredient | 3A | 3B |
|---|---|---|
| Ethanol, USP 190 proof | 15.0 | 15.0 |
| Glycerin | 7.5 | 7.5 |
| Polysorbate 80, NF | 0.12 | 0.12 |
| Flavor | 0.16 | 0.16 |
| Saccharin Sodium | 0.067 | 0.067 |
| Color Solution | 0.04 | 0.04 |
| G-180 Coolant (7.5% solution)[4] | 0.03 | 0.03 |
| Calcium Chloride | 0.025 | 0.025 |
| Cetylpyridinium Chloride | 0.045 | 0.045 |
| Benzoic Acid | 0.005 | 0.005 |
| Sodium Benzoate | 0.054 | 0.054 |
| Mirapol ® A 15[5] | 0.05 | 0.1 |
| Water | QS | QS |

[4] Available from Givaudan of Cincinnati, OH
[5] Available from Rhodia, Cranbury, New Jersey Assay for Taste Receptors Human fungiform taste bud cells were isolated from tongues of humans as described in Ozdener, Mehmet, and Nancy Rawson. "Primary Culture of Mammalian Taste Epithelium." *Methods in Molecular Biology;* 2013; 945: 95-107.

Then the cells were further cultured according to the following procedure. The cells were grown in a Corning® cell culture flask, with a surface area of 75 cm$^2$, a canted neck, and a 0.2 µm Vent cap (Catalog#430641, available from VWR International, Bridgeport, N.J., USA) at 37° C. using a growth medium containing 500 mL of Iscove's Modified Dulbecco's Media (IMDM), 100 mL of Ham's F12 Nutrient Mixture, 60 mL Fetal Bovine Serum (FBS), and 150 µg/mL Penicillin-Streptomycin cocktail (all growth media components available from Life Technologies, Grand Island, N.Y., USA).

After the cells reach 80-90% confluence, which generally takes about seven days of cultivation, the cells were released by adding 3 mL of Gibco® Trypsin-EDTA (0.05%) solution (available from Life Technologies) at 37° C. in couple of minutes, followed by adding 12 mL of cell growth medium to deactivate trypsin. Then the cells were diluted in the growth medium at approximately 250,000 cells/mL. Next, 100 µl volume of cell suspension containing 20,000 to 30,000 cells were seeded into each well of a Falcon® 96 Well Black with Clear Flat Bottom TC-Treated Imaging Plate (REF #353219, available from VWR International, Bridgeport, N.J., USA) and the cells are grown overnight.

After the overnight cultivation, the cell culture media was removed by aspiration. Then, 100 µL of Calcium-6QF solution was added to each well. The Calcium-6QF solution was made by dissolving the contents of one vial of Calcium-6QF (available from Molecular Devices, Sunnyvale, Calif., USA) in 20 mL of assay buffer, which contains Hank's Balanced Salt Solution (HBSS) with 20 mM HEPES (4-(2-hydroxyethyl)-1-piperazineethanesulfonic acid) (both components are available from Life Technologies). The plate was then incubated at 37° C. for 105 min and at room temperature for 15 min. Then the 96-well plate is placed in a FLIPR® Tetra High Throughput Cellular Screening System (available from Molecular Devices) and 20 µL of working solution, as described below, are added to each well. The fluorescence signal was read continuously for 5 min, where the excitation and emission wave lengths used were 488 nM and 510 nM respectively. The peak value and/or area under the curve after five minutes was calculated and recorded.

In order to form the working solution, the test material was diluted with the assay buffer. Examples of test materials can include, but are not limited to GG solutions, PG solutions, 1,3-PPD solutions, full formulations such as those in Example 4 and 5, and combinations thereof. The amount of assay buffer varies depending on the desired final concentration, which occurs when the test material is in the wells. For example, if the test material is GG, it can be desirable to have a final concentration of 2 mM. Thus, a 12 mM working solution is made and when it is added to the wells, the concentration is further reduced to a final concentration of 2 mM. In another example, in order to make a working solution for Examples 4 and 5, and other full formulations, 1 mL of the example is added to 27 mL of assay buffer to form the working solution and then it is added to the wells for an overall reduction of 162 fold.

While the specification concludes with the claims particularly pointing and distinctly claiming the invention, it is believed that embodiments of the present invention will be better understood from this description. In all embodiments of the present invention, all weight percentages are by weight of the total composition, unless specifically stated otherwise. All ratios are weight ratios, unless specifically stated otherwise. All ranges are inclusive and combinable. The number of significant digits conveys neither limitation on the indicated amounts nor on the accuracy of the measurements. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition with reduced bitterness comprising:
   a. a polyquaternium selected from the group consisting of polyquaternium-2, polyquaternium-17, polyquternium-18, and combinations thereof;
   b. a fluoride compound;
   c. a metal salt;
   wherein the oral care composition is a dentifrice.

2. The oral care composition of claim 1 further comprising hops.

3. The oral care composition of claim 1 wherein the fluoride compound comprises stannous fluoride.

4. The oral care composition of claim 1 wherein the metal salt comprises zinc.

5. The oral care composition of claim 1 wherein an overall bitterness is reduced by at least about 25% as compared to an identical composition without the polyquaternium as determined by the in vitro Assay for Taste Receptors.

6. The oral care composition of claim 1 wherein an overall bitterness is less than about 6000 fluorescence units as determined by the in vitro Assay for Taste Receptors.

7. The oral care composition of claim 1 further comprising an abrasive polishing material.

8. The oral composition of claim 1 further comprising a surfactant.

9. The oral composition of claim 1 further comprising a bleaching agent.

10. The oral care composition of claim 1 further comprising a flavor or a flavor component.

11. An oral care composition with reduced bitterness comprising:
    a. a polyquaternium selected from the group consisting of polyquaternium-2, polyquaternium-17, polyquternium-18, and combinations thereof;
    b. a bitter agent wherein the bitter agent is a fluoride ion source selected from the group consisting of stannous fluoride, sodium fluoride, fluorophosphates, amine fluoride, and combinations thereof.

12. The oral care composition of claim 11 wherein the oral care composition is selected from the group consisting of dentifrice, mouthwash, whitening gel, denture cream, and combinations thereof.

13. The oral care composition of claim 11 wherein the composition further comprises an additional bitter agent wherein the additional bitter agent is an antimicrobial agent selected from the group consisting of cetyl pyridinium chloride, hops, zinc salt, peroxide, and combinations thereof.

14. The oral care composition of claim 13, wherein the antimicrobial is the zinc salt selected from the group consisting zinc chloride, zinc citrate, zinc oxide, zinc oxalate, zinc gluconate, zinc lactate, and combinations thereof.

15. The oral care composition of claim 11 wherein the composition further comprises an additional bitter agent wherein the bitter agent is a solvent selected from the group consisting of propylene glycol, sorbitol, glycerin, xylitol, and combinations thereof.

16. The oral care composition of claim 11 wherein the composition further comprises an additional the bitter agent wherein the additional bitter agent is a surfactant selected from the group consisting of sodium lauryl sulfate, cocoamidylpropyl betaine, alkyl phosphates, and combinations thereof.

17. The oral care composition of claim 11 wherein the fluoride ion source comprises stannous fluoride.

18. The oral care composition of claim 11 further comprising a flavor or a flavor component.

19. The oral care composition of claim 11 wherein an overall bitterness is reduced by at least about 30% as compared to an identical composition without the polyquaternium as determined by the in vitro Assay for Taste Receptors.

20. The oral care composition of claim 11 wherein an overall bitterness is less than about 7000 fluorescence units as determined by the in vitro Assay for Taste Receptors.

* * * * *